(12) United States Patent
Zhu et al.

(10) Patent No.: US 6,514,737 B1
(45) Date of Patent: Feb. 4, 2003

(54) **METHOD FOR CLONING AND EXPRESSION OF ASISI RESTRICTION ENDONUCLEASE AND ASISI METHYLASE IN *E. COLI***

(75) Inventors: Zhenyu Zhu, Beverly, MA (US); Shuang-yong Xu, Lexington, MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 09/933,313

(22) Filed: Aug. 20, 2001

(51) Int. Cl.[7] .................................................. C12N 9/12
(52) U.S. Cl. ....................................................... 435/194
(58) Field of Search .............................. 435/199, 320.1, 435/252.3; 536/23.2

(56) References Cited

U.S. PATENT DOCUMENTS

| | | | |
|---|---|---|---|
| 5,200,333 A | 4/1993 | Wilson | 435/172.3 |
| 5,498,535 A | 3/1996 | Fomenkov et al. | 435/172.3 |

OTHER PUBLICATIONS

Roberts and Macelis, Nucl. Acids Res. 27: 312–313, (1999).
Kosykh et al., Mol. Gen. Genet. 178: 717–719, (1980).
Mann et al., Gene 3: 97–112, (1978).
Walder et al., Proc. Nat. Acad. Sci. 78: 1503–1507, (1981).
Bougueleret al., Nucl. Acids. Res. 12: 3659–3676, (1984).
Gingeras and Brooks, Proc. Natl. Acad. Sci. USA 80: 402–406, (1983).
Theriault and Roy, Gene 19: 355–359, (1982).
Blumenthal et al., J. Bacteriol. 164: 501–509, (1985).
Wayne et al., Gene 202: 83–88, (1997).
Kiss et al., Nucl. Acids. Res. 13: 6403–6421, (1985).
Szomolanyi et al., Gene 10: 219–225, (1980).
Janulaitis et al., Gene 20: 197–204, (1982).
Kiss and Baldauf, Gene 21: 111–119, (1983).
Walder et al., J. Biol. Chem. 258: 1235–1241, (1983).
Fomenkov et al., Nucl. Acids. Res. 22: 2399–2403, (1994).
Malone et al., J. Mol. Biol. 253: 618–632, (1995).
New England Biolabs' Catalog, p. 220, (2000–2001).
New England Biolabs' Catalog, p. 272, (2000–2001).

*Primary Examiner*—Charles Patterson, Jr.
(74) *Attorney, Agent, or Firm*—Gregory D. Williams (57) ABSTRACT

The present invention relates to recombinant DNA which encodes the AsiSI restriction endonuclease as well as AsiSI methylase, expression of AsiSI restriction endonuclease and AsiSI methylase in *E. coli* cells containing the recombinant DNA.

6 Claims, 4 Drawing Sheets

FIG. 1 asiSIR: AsiSI restriction endonuclease gene
asiSIM: AsiSI methylase gene
Pilus: Pilus assembly protein gene

FIG. 2

```
     GTGAATCGCGCAACTGCGGTCGAATTGTTTGCGGGCTGTGGGGGGCTATCGACCGGACTG
  1  ------------------------------------------------------------  60
     M  N  R  A  T  A  V  E  L  F  A  G  C  G  G  L  S  T  G  L

TTGGACGCTGGCTACGACGTGCGTCTGGGTGTCGACAACAATGCCCCAAGTTTGGTCGCC
 61  ------------------------------------------------------------ 120
     L  D  A  G  Y  D  V  R  L  G  V  D  N  N  A  P  S  L  V  A

TATGATTACAACCATGCCTATCGGGGGTCAAAGTCACTACTCCGCGATGTTAGTGCCTTA
121  ------------------------------------------------------------ 180
     Y  D  Y  N  H  A  Y  R  G  S  K  S  L  L  R  D  V  S  A  L

AGGGGACCCGAACTACTGGAAGCCGCAGGAGTCGACTCGATTGACGTACTCTCCGGCGGG
181  ------------------------------------------------------------ 240
     R  G  P  E  L  L  E  A  A  G  V  D  S  I  D  V  L  S  G  G

CCGCCCTGCCAGCCCTTTTCGATAGCCGGGAAGCGACTGGGGCTTGACGATCCTCGAGGG
241  ------------------------------------------------------------ 300
     P  P  C  Q  P  F  S  I  A  G  K  R  L  G  L  D  D  P  R  G

CACCTTATTGCGGAATTTGTCCGGATTGTAGACGAAGTTCGGCCGAAGGCGGTCGTGTTT
301  ------------------------------------------------------------ 360
     H  L  I  A  E  F  V  R  I  V  D  E  V  R  P  K  A  V  V  F

GAAAACGTACCTGCACTGCAAACTTCGCATAATGGAGATGTAGTTCGCGCAACAACTGAC
361  ------------------------------------------------------------ 420
     E  N  V  P  A  L  Q  T  S  H  N  G  D  V  V  R  A  T  T  D

GCGCTTGAGCAGCTTGGCTACGGGGTAAGACGCGCAATCCTCAACGCGGCCGACTGGGGT
421  ------------------------------------------------------------ 480
     A  L  E  Q  L  G  Y  G  V  R  R  A  I  L  N  A  A  D  W  G

GTCCCGCAGGCGCGCAAGCGATTGATCCTGATTGCTGTGCGCGACGTAGCAGAGTTTTCG
481  ------------------------------------------------------------ 540
     V  P  Q  A  R  K  R  L  I  L  I  A  V  R  D  V  A  E  F  S

TTCCCGCCTAAGCCGACTCACTCAGGCGACCCGTCTGGGAGCCTTCGGCCCTACCGAACA
541  ------------------------------------------------------------ 600
     F  P  P  K  P  T  H  S  G  D  P  S  G  S  L  R  P  Y  R  T

GCTTCGGATGCTCTATGGGACCTGCCTGACGTGAACACGGATGCTGCCCGTGAGATACCG
601  ------------------------------------------------------------ 660
     A  S  D  A  L  W  D  L  P  D  V  N  T  D  A  A  R  E  I  P

AACCACGAACCGACTGCCCATTCGCCCGCGATGCTCAAGGCTTTCGCCGGACTAGAACCG
661  ------------------------------------------------------------ 720
     N  H  E  P  T  A  H  S  P  A  M  L  K  A  F  A  G  L  E  P

GGGAAGCGTGAACCGAAGTCGCGGCACGACAGGCTGCATCCCGACCGCCCGGGGTATACT
721  ------------------------------------------------------------ 780
     G  K  R  E  P  K  S  R  H  D  R  L  H  P  D  R  P  G  Y  T

CTTCGCGCAGGCTCTGGCAACTTCTCACCAATGAGGCCGATCCATTATGAGTTTGATCGG
781  ------------------------------------------------------------ 840
     L  R  A  G  S  G  N  F  S  P  M  R  P  I  H  Y  E  F  D  R

GTGATTTCGGTTCGAGAGAGTGCTCGGTTACAGGGCTTTAGCGATGACTTCATCTGGCCG
841  ------------------------------------------------------------ 900
     V  I  S  V  R  E  S  A  R  L  Q  G  F  S  D  D  F  I  W  P

GACAGCCTGTCCAGACTTCAACAATACCGTCAAGTTGGAAACGCTGTTCCGCCAGCTCTT
901  ------------------------------------------------------------ 960
     D  S  L  S  R  L  Q  Q  Y  R  Q  V  G  N  A  V  P  P  A  L

GGGGAGGTGGTCGGGCGACACGTTGCGTCGATTCTGGGATTTGACCTTGATGCTGATTCA
961  ------------------------------------------------------------ 1020
     G  E  V  V  G  R  H  V  A  S  I  L  G  F  D  L  D  A  D  S

GCAGCGGGAGACCCTGCTTCGCGGCCGAATCCGTTCAACTTCACACACGAAGAGCGTGCA
1021 ------------------------------------------------------------ 1080
     A  A  G  D  P  A  S  R  P  N  P  F  N  F  T  H  E  E  R  A

GCTCGACGGGCGCGTTACCACCGGGGTGGAGCGAGTTTCGGATCGGCCAACGGAGCGTCC
1081 ------------------------------------------------------------ 1140
     A  R  R  A  R  Y  H  R  G  G  A  S  F  G  S  A  N  G  A  S

GACTCCTCGGAAGTAGTGGCCTCGATCGTATGA
1141 --------------------------------- 1173
     D  S  S  E  V  V  A  S  I  V  *
```

FIG. 3

```
    ATGGGCGAGTCTATTGATCAATTAAACCCTATCTCCGGGGACGGTCGCCTCCTGCAATCT
1   ------------+---------+---------+---------+---------+---------+   60
    M  G  E  S  I  D  Q  L  N  P  I  S  G  D  G  R  L  L  Q  S

CACGGTCTGACCAGCAAGGTATACGTTCCGATATTGCGATACGTGTTTGCGCTTCGCTAC
61  ------------+---------+---------+---------+---------+---------+  120
    H  G  L  T  S  K  V  Y  V  P  I  L  R  Y  V  F  A  L  R  Y

AAAACTGGCGACACGGTCGTCGAATTCACCCTTGATGACATAAGGGACGCGGCTGCGGCC
121 ------------+---------+---------+---------+---------+---------+  180
    K  T  G  D  T  V  V  E  F  T  L  D  D  I  R  D  A  A  A  A

CTGGGTATAGTGGTACGTAATGCCGCTGACGTGATATATAGGATGAGATCACGCACCGTC
181 ------------+---------+---------+---------+---------+---------+  240
    L  G  I  V  V  R  N  A  A  D  V  I  Y  R  M  R  S  R  T  V

CTTCCGGCTGAGATCCTTGAGCTTGGGTTTTACGTCCTCACACAAGCTGGTCGAGGCCGC
241 ------------+---------+---------+---------+---------+---------+  300
    L  P  A  E  I  L  E  L  G  F  Y  V  L  T  Q  A  G  R  G  R

TATCGATTTGAGCAGGCATCCAGCACTGTTATCGACCTACCTAATACAAGGCCAATAGAA
301 ------------+---------+---------+---------+---------+---------+  360
    Y  R  F  E  Q  A  S  S  T  V  I  D  L  P  N  T  R  P  I  E

GCCCTCGACTTGACACCAAACCCCGTTCGACGTTTACTCCCAGAACACTTAGCCGACATG
361 ------------+---------+---------+---------+---------+---------+  420
    A  L  D  L  T  P  N  P  V  R  R  L  L  P  E  H  L  A  D  M

GATGAGCAGGCGATTCTGATGGTCGCCGGATACTGCAATCTGTGGCAGCATTTCACAGGG
421 ------------+---------+---------+---------+---------+---------+  480
    D  E  Q  A  I  L  M  V  A  G  Y  C  N  L  W  Q  H  F  T  G

CTTACAGTCTACCGGCTGCGTTCTCATGTCCGAAAAAGTGTGCCTGGAGTGGGTCAAGCG
481 ------------+---------+---------+---------+---------+---------+  540
    L  T  V  Y  R  L  R  S  H  V  R  K  S  V  P  G  V  G  Q  A

GAACTAGACGAAGTGAACGTGGCGGTCGCGGTACGGGATGACGAGGTGCCGGTGATCATC
541 ------------+---------+---------+---------+---------+---------+  600
    E  L  D  E  V  N  V  A  V  A  V  R  D  D  E  V  P  V  I  I

CCAGTCGAAGCGAAGGCTGTCGCGGATCCGGTGAACCGAGTACAGATTGCAACTCAGGTT
601 ------------+---------+---------+---------+---------+---------+  660
    P  V  E  A  K  A  V  A  D  P  V  N  R  V  Q  I  A  T  Q  V

GCCTTCGCGAACCGGTATTTTGCTGAGCACGAATTTCGCCCAATGACTATCAAAGTCGAT
661 ------------+---------+---------+---------+---------+---------+  720
    A  F  A  N  R  Y  F  A  E  H  E  F  R  P  M  T  I  K  V  D

CGGGATAGTGTCCTCAATCTGCTCGAATTTAATGCCACCCCTATTGCAAGCGAGATAGAG
721 ------------+---------+---------+---------+---------+---------+  780
    R  D  S  V  L  N  L  L  E  F  N  A  T  P  I  A  S  E  I  E

GTTATTCGGTCAGCTAGATACCGCCTCATTCTCTCCGACAGACAGCGCCACCTTATCGAC
781 ------------+---------+---------+---------+---------+---------+  840
    V  I  R  S  A  R  Y  R  L  I  L  S  D  R  Q  R  H  L  I  D

GAAACAGACCAGGTGATGTTGTGA
841 ------------+---------+----  864
    E  T  D  Q  V  M  L  *
```

METHOD FOR CLONING AND EXPRESSION OF ASISI RESTRICTION ENDONUCLEASE AND ASISI METHYLASE IN *E. COLI*

BACKGROUND OF THE INVENTION

The present invention relates to recombinant DNA encoding the AsiSI restriction endonuclease (endonuclease) as well as AsiSI methyltransferase (methylase), expression of AsiSI restriction endonuclease and methylase in *E. coli* cells containing the recombinant DNA.

AsiSI endonuclease is found in the strain of Arthrobacter species S (New England Biolabs' strain collection #1221). It recognizes the double-stranded DNA sequence 5'GCGAT/CGC3' (SEQ ID NO:1) and cleaves between the T and C to generate a 2-base 3' overhanging ends (/indicates the cleavage of phosphodiester bond). AsiSI methylase (M.AsiSI) is also found in the same strain. It recognizes the double-stranded DNA sequence 5'GCGATCGC 3' (SEQ ID NO:1) and presumably modifies the C5 position of cytosine at base number 2, or number 6, or number 8. The 5mC modified AsiSI site is resistant to AsiSI restriction digestion.

Type II restriction endonucleases are a class of enzymes that occur naturally in bacteria and in some viruses. When they are purified away from other bacterial/viral proteins, restriction endonucleases can be used in the laboratory to cleave DNA molecules into small fragments for molecular cloning and gene characterization.

Restriction endonucleases recognize and bind particular sequences of nucleotides (the 'recognition sequence') on DNA molecules. Once bound, they cleave the molecule within (e.g. BamHI), to one side of (e.g. SapI), or to both sides (e.g. TspRI) of the recognition sequence. Different restriction endonucleases have affinity for different recognition sequences. Over two hundred and eleven restriction endonucleases with unique specificities have been identified among the many hundreds of bacterial species that have been examined to date (Roberts and Macelis, Nucl. Acids Res. 27:312–313, (1999)).

Restriction endonucleases typically are named according to the bacteria from which they are discovered. Thus, the species Deinococcus radiophilus for example, produces three different restriction endonucleases, named DraI, DraII and DraIII. These enzymes recognize and cleave the sequences 5'TTT/AAA3' (SEQ ID NO:2), 5'PuG/GNCCPy3' (SEQ ID NO:29) and 5'CACNNN/GTG3' (SEQ ID NO:3) respectively. *Escherichia coli* RY13, on the other hand, produces only one enzyme, EcoRI, which recognizes the sequence 5'G/AATTC3' (SEQ ID NO:4).

A second component of bacterial/viral restriction-modification (R-M) systems are the methylase. These enzymes co-exist with restriction endonucleases and they provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. Only unmodified, and therefore identifiably foreign DNA, is sensitive to restriction endonuclease recognition and cleavage. During and after DNA replication, usually the hemi-methylated DNA (DNA methylated on one strand) is also resistant to the cognate restriction digestion.

With the advancement of recombinant DNA technology, it is now possible to clone genes and overproduce the enzymes in large quantities. The key to isolating clones of restriction endonuclease genes is to develop an efficient method to identify such clones within genomic DNA libraries, i.e. populations of clones derived by 'shotgun' procedures, when they occur at frequencies as low as $10^{-3}$ to $10^{-4}$. Preferably, the method should be selective, such that the unwanted clones with non-methylase inserts are destroyed while the desirable rare clones survive.

A large number of type II restriction-modification systems have been cloned. The first cloning method used bacteriophage infection as a means of identifying or selecting restriction endonuclease clones (EcoRII: Kosykh et al., Mol. Gen. Genet. 178: 717–719, (1980); HhaII: Mann et al., Gene 3: 97–112, (1978); PstI: Walder et al., Proc. Nat. Acad. Sci. 78: 1503–1507, (1981)). Since the expression of restriction-modification systems in bacteria enable them to resist infection by bacteriophage, cells that carry cloned restriction-modification genes can, in principle, be selectively isolated as survivors from genomic DNA libraries that have been exposed to phage. However, this method has been found to have only a limited success rate. Specifically, it has been found that cloned restriction-modification genes do not always confer sufficient phage resistance to achieve selective survival.

Another cloning approach involves transferring systems initially characterized as plasmid-borne into *E. coli* cloning vectors (EcoRV: Bougueleret et al., Nucl. Acids. Res. 12: 3659–3676, (1984); PaeR7: Gingeras and Brooks, Proc. Natl. Acad. Sci. USA 80:402–406, (1983); Theriault and Roy, Gene 19:355–359 (1982); PvuII: Blumenthal et al., J. Bacteriol. 164:501–509, (1985); Tsp45I: Wayne et al. Gene 202:83–88, (1997)).

A third approach is to select for active expression of methylase genes (methylase selection) (U.S. Pat. No. 5,200,333 and BsuRI: Kiss et al., Nucl. Acids. Res. 13:6403–6421, (1985)). Since restriction-modification genes are often closely linked together, both genes can often be cloned simultaneously. This selection does not always yield a complete restriction system however, but instead yields only the methylase gene (BspRI: Szomolanyi et al., Gene 10:219–225, (1980); BcnI: Janulaitis et al., Gene 20:197–204 (1982); BsuRI: Kiss and Baidauf, Gene 21:111–119, (1983); and MspI: Walder et al., J. Biol. Chem. 258:1235–1241, (1983)).

A more recent method, the "endo-blue method", has been described for direct cloning of thermostable restriction endonuclease genes into *E. coli* based on the indicator strain of *E. coli* containing the dinD::lacZ fusion (Fomenkov et al., U.S. Pat. No. 5,498,535; Fomenkov et al., Nucl. Acids Res. 22:2399–2403, (1994)). This method utilizes the *E. coli* SOS response signals following DNA damage caused by restriction endonucleases or non-specific nucleases. A number of thermostable nuclease genes (TaqI, Tth111I, BsoBI, Tf nuclease) have been cloned by this method (U.S. Pat. No. 5,498,535). The disadvantage of this method is that sometimes positive blue clones containing a restriction endonuclease gene are difficult to culture due to the lack of the cognate methylase gene.

There are three major groups of DNA methylases based on the position and the base that is modified (C5 cytosine methylases, N4 cytosine methylases, and N6 adenine methylases). N4 cytosine and N6 adenine methylases are amino-methyltransferases (Malone et al. J. Mol. Biol. 253:618–632, (1995)). When a restriction site on DNA is modified (methylated) by the methylase, it is resistant to digestion by the cognate restriction endonuclease. Sometimes methylation by a non-cognate methylase can also confer the DNA site resistant to restriction digestion. For example, Dcm methylase modification of 5'CCWGG3' (W=A or T) (SEQ ID NO:5) can also make the DNA resistant to PspGI restriction digestion. Another example is that CpG methylase can modify the CG dinucloetide and make the NotI site (5'GCGGCCGC3' (SEQ ID NO:6)) refractory to NotI digestion (New England Biolabs' Catalog, 2000–01, page 220). Therefore methylases can be used as a tool to modify certain DNA sequences and make them uncleavable by restriction enzymes.

Because purified restriction endonucleases and modification methylases are useful tools for creating recombinant molecules in the laboratory, there is a great commercial interest to obtain bacterial strains through recombinant DNA techniques that produce large quantities of restriction enzymes. Such over-expression strains should also simplify the task of enzyme purification.

SUMMARY OF THE INVENTION

The present invention relates to a method for cloning the AsiSI restriction endonuclease from Arthrobacter species S into E. coli by methylase selection and inverse PCR amplification of the adjacent DNA.

The cloning of AsiSI endonuclease and methylase genes proved to be extremely difficult. No M.AsiSI positive clones were identified in a Sau3AI partial genomic DNA library. Neither were M.AsiSI positive clones identified in AatII, AccI, Af/III, KasI, NdeI, and XmaI genomic libraries using methylase selection. The difficulty may result from poor expression of asiSIM gene in E. coli and/or cross contamination of other common cloning vectors such as pUC18, pUC19, and pBR322 (Ap$^R$) that do not harbor AsiSI sites.

Since the typical methylase selection did not yield any positive clones initially, a second cloning strategy was attempted by direct PCR with primers based on the conserved regions of C5 methylases. There are ten highly conserved amino acid regions within most of C5 methylases. Degenerate primers were synthesized based on the conserved motifs I and VI. PCR was attempted to amplify part of the asiSIM gene. Three PCR products of different sizes were found, gel-purified, and sequenced, but none of them contained conserved C5 methylase motifs.

A third successful cloning strategy involved construction of a vector with pUC19 origin and Km$^R$, containing a single AsiSI site within the Km resistance gene (pUCKm). It was expected that modification of the AsiSI site within the Km$^R$ gene would render the plasmid intact following AsiSI digestion, thus giving rise to Km$^R$ colonies. If the AsiSI site within the Km$^R$ gene is not modified, the plasmid would be cleaved by AsiSI and lost during transformation. As a result, no Km$^R$ colony formation would be detected. The Km$^R$ selection marker also solved the problem of contamination by Ap$^R$ cloning vectors. NlaIII partial genomic DNA library was constructed and challenged with AsiSI or SgfI (SgfI is an isoschizomer of AsiSI). Following methylase gene selection four AsiSI-resistant clones were identified. DNA sequencing indicated that the cloned methylase gene encoded a C5 methylase and displayed high homology to other C5 methylases.

Since restriction genes are usually located in close proximity with methylase gene, inverse PCR was employed to clone the adjacent DNA surrounding the asiSIM gene. Open reading frames (ORF) were identified on both sides of the asisIM gene. The downstream ORF was found to be homologous to a pilus assembly protein, thus it was predicted that this was not the asiSIR gene. The upstream ORF did not show significant homology to any gene in Genbank. In the first expression strategy, both the asiSIR and asiSIM genes were amplified by PCR and cloned in a T7 expression vector. Clones with inserts were identified, but no AsiSI activity was detected in cell extract. The second expression strategy used two-plasmid expression system. The asiSIM gene was first cloned in pACYC184 to premodify expression host ER2566, and the putative asiSIR gene was cloned in a T7 vector pET21at. AsiSI activity was detected in IPTG-induced cell extracts. This ORF was named as asiSIR. Three clones with high AsiSI activity were sequenced and one confirmed to be the wild type sequence.

BRIEF DESCRIPTION OF THE DRAWINGS

FIG. 2. DNA sequence of AsiSI methylase gene (AsiSIM, 1164 bp) (SEQ ID NO:7) and its encoded amino acid sequence (SEQ ID NO:8).

FIG. 3. DNA sequence of AsiSI endonuclease gene (AsiSIR, 867 bp) (SEQ ID NO:9) and its encoded amino acid sequence (SEQ ID NO:10).

DETAILED DESCRIPTION OF THE INVENTION

Figure 1:
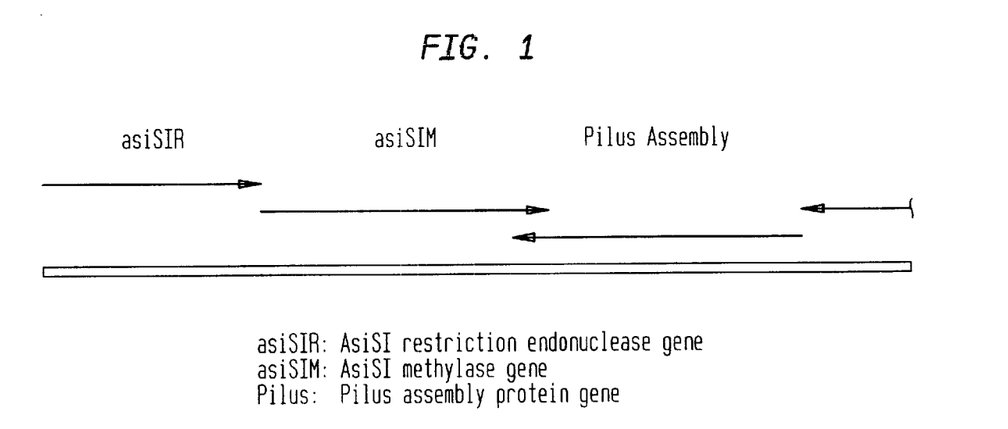
FIG. 1. Gene organization of AsiSI restriction-modification system. asiSIR, AsiSI restriction endonuclease gene; asiSIM, AsiSI methylase gene.
Figure 4:
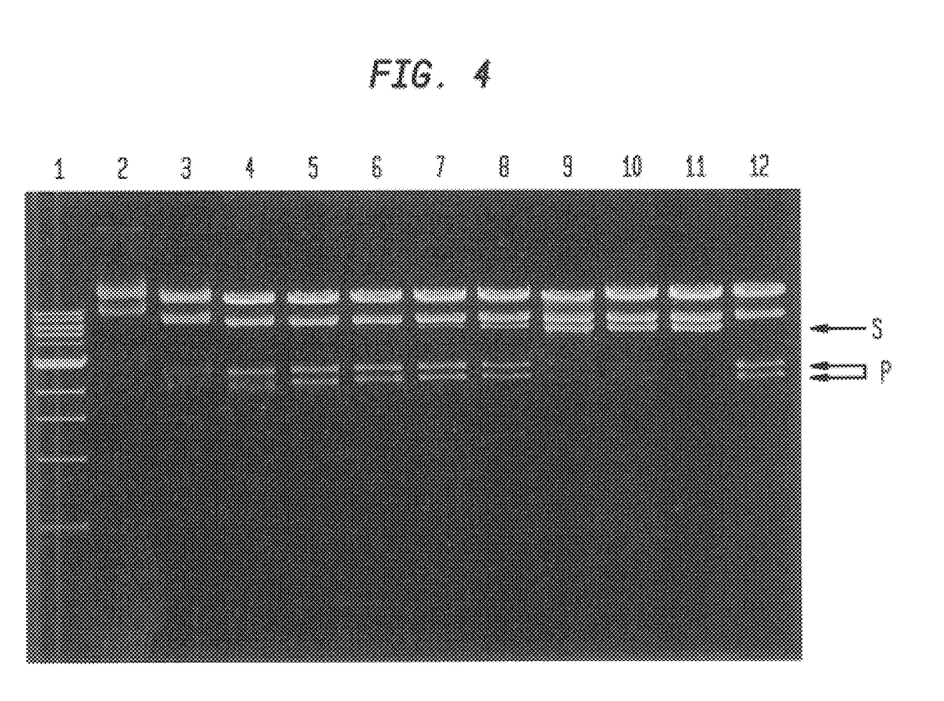
FIG. 4. Recombinant AsiSI restriction endonuclease activity in cell extract. Lane 1, 1 kb Marker; lane 12, XhoI digested pUC-Adenovirus (XbaI fragment) DNA cut by native SgfI, an isoschizomer of AsiSI, lanes 2 to 11, XhoI digested pUC-Adenovirus (XbaI fragment) DNA treated with cell extract containing recombinant AsiSI restriction endonuclease; The dilution factors in lanes 2 to 11 are: 1, 2, 4, 8, 16, 32, 64, 128, 256, 512. S=substrate fragment; P=cleavage products.

The present invention relates to recombinant DNA which encodes the AsiSI restriction endonuclease, as well as to methods for producing recombinant AsiSI.

The cloning of AsiSI restriction and modification system proved to be very difficult. One of the major problems was isolation of plasmids in challenged library that have lost AsiSI sites or from contaminating plasmids that do not have any AsiSI sites. The most common cloning vectors such as pUC18, pUC19, pBR322, pLITMUS do not contain AsiSI site. Any contaminating plasmid DNA would be amplified in the library following methylase selection.

Since there are no AsiSI sites in the cloning vector such as pRRS (a pUC19 derivative), efforts were made to insert two AsiSI sites in pRRS. A small DraI fragment (18 bp) of pRRS was first deleted and a DNA linker containing PmeI site was inserted. A DNA linker containing the sequence 5' AAGCGATCGCTT 3' (SEQ ID NO:11) was inserted in the PmeI site and the same linker was also inserted in the SspI site. The resulting plasmid contained two AsiSI sites.

AsiSI genomic DNA was partially digested with Sau3AI and DNA fragment between 2–10 kb was gel-purified and then ligated to BamHI digested and CIP treated pRRS (2AsiSI). The ligated DNA was used to transform ER2502.

Plasmid DNA was prepared from amplified transformants and challenged with AsiSI. Following AsiSI digestion, the DNA mixture was transformed back into ER2502 cells. Transformants were screened for resistance to AsiSI digestion. Nine out of 36 screened were resistant to AsiSI digestion, but none of them contained AsiSI methylase gene.

Methylase selection was also performed for AatII, AccI, AflIII, KasI, NdeI, and XmaI genomic DNA libraries. Again AsiSI resistant clones were identified, but no conserved methylase motifs were found in DNA sequence analysis.

Since the typical methylase selection did not work initially, other cloning strategy was attempted to clone the asiSIM gene. Degenerate primers were synthesized based on the conserved C5 methylase motif I (amino acid sequence LFAGIG (SEQ ID NO:12) or LFSGIG (SEQ ID NO:13)) and motif VI (amino acid sequence ENVRGL (SEQ ID NO:14)). PCR was attempted to amplify part of the asiSIM gene. Three PCR products of different sizes were found, gel-purified, and sequenced. Translation of the DNA sequences and comparison with known methylase genes in GenBank indicated that none of them contained conserved C5 methylase motifs.

The method that was successfully used to clone asiSIM gene took advantage of an AsiSI site in the $KM^R$ gene. A cloning vector with $Km^R$ selection marker and pUC19 origin (ColEI) was constructed and then used as the vector for genomic library construction and methylase selction. This $Km^R$ selection vector solved the contamination problem resulted from the most common $Ap^R$ cloning vectors. The existing AsiSI site in the $Km^R$ selection marker further increased the methylase selection efficiency.

After the asiSIM and asiSIR genes were sequenced, the asiSIM and asiSIR genes were amplified by PCR and cloned into a T7 expression vector pET21a. Recombinant plasmids with insert were identified, but no AsiSI activity was detected in IPTG-induced cell extracts. It may be necessary to express asiSIM and asiSIR genes separately in two plasmids.

The method described herein by which the asiSIM and asiSIR genes are preferably cloned and expressed in E. coli using the following steps:

1. Construction of Cloning Vector pUCKm

The cloning vector pUCKm was constructed by combining the origin and multiple cloning site of pUC19 and the kanamycin resistance gene of pGPS3 (NEB catalog, page 272, 2000–2001). The resulting plasmid is named as pUCKm, which is a high copy number plasmid with $Km^R$ instead of the original $Ap^R$. Most of the multiple cloning sites were kept as unique sites.

2. Construction of Genomic DNA Libraries and Methylase Selection

Genomic DNA was prepared from Arthrobacter species S and partially digested with restriction enzyme NlaIII or any isoschizomers. The restricted genomic DNA was ligated to cloning vector pUCKm (digested with SphI and treated with CIP). The ligated DNA was transformed into restriction minus E. coli competent cell ER2502 and transformants were pooled and amplified. Plasmid DNA libraries were prepared and challenged with AsiSI or SgfI. The DNA ends were destroyed by Mung bean nuclease. Following digestion, the plasmids were transformed back into ER2502. $Km^R$ survivors were screened for resistance to SgfI digestion. The resistant clones were identified as methylase positive clones. Sequencing the insert verified the cloning of a C5 methylase gene.

3. Sequencing of AsiSIM Gene

The asiSIM gene was sequenced using forward and reverse primers for pUC19 multiple cloning sites and by primer walking. The asiSIM gene is 1173 bp, encoding a 390-amino acid protein with predicted molecular mass of 42.1 kDa.

4. Cloning of asiSIR Gene by Inverse PCR

The Genomic DNA was digested with 4–6 bp cutting restriction enzymes such as AgeI, BamHI, BsawI, BspEI, BsrFI, BstYI, KasI, NruI, NspI, PstI, PvuI, SacI, SphI, XmaI. The digested DNA was self-ligated at a low DNA concentration and then used for inverse PCR amplification of the adjacent DNA. Inverse PCR products were derived, gel-purified and sequenced. An ORF of 864 bp was found upstream of the asiSIM gene. This ORF was predicted to be the asiSIR gene. Expression of this ORF confirmed the above prediction (see below, section 10). This ORF encodes a 287-aa protein with predicted molecular mass of 32.3 kDa.

5. Cloning of AsiSIM Gene into pACYC184 to Construct a Premodified Host

The AsiSIM gene was amplified from the genomic DNA by PCR using two primers. The PCR DNA was digested with BamHI and SphI and ligated to a low-copy-number plasmid pACYC184 that is compatible with pET T7 expression vector. The premodified host ER2566 [pACYC-AsiSIM] was used for expression of the AsiSIR gene in E. coli.

6. Expression of asiSIR Gene in T7 Expression Vector pET21at

An NdeI and HindIII fragment containing the asiSIR gene was cloned into pET2 at expression vector. The ligated recombinant DNA was transformed into premodified host ER2566 [pACYC-AsiSIM]. The APR CmR transformants were induced with IPTG. Recombinant AsiSI activity was detected in cell extract. Plasmids were extracted from those clones with high activity. After sequencing, one clone with wild type sequence (#28) was used for further study on stability and large scale purification of AsiSI.

7. Purification of AsiSI Endonuclease by Chromatography

Cell extract containing the recombinant AsiSI endonuclease was purified by chromatography through Heparin-Sepharose and DEAE-Sepharose columns. Alternatively, AsiSI endonuclease can be purified by chromatography through cation/anion exchange columns and gel filtration sizing columns or by affinity purification through fusion tags.

The present invention is further illustrated by the following Example. This Example is provided to aid in the understanding of the invention and is not construed as a limitation thereof.

The references cited above and below are herein incorporated by reference.

EXAMPLE I

Cloning of AsiSI Restriction-modification System in E. coli

1. Construction of Two Cloning Vectors

Two cloning vectors were constructed for cloning of AsiSI R-M genes. The first plasmid was PRRS vector with the insertion of two AsiSI site. The two AsiSI sites were inserted upstream and down stream of the ampicillin resistance gene. If the plasmid was digested with AsiSI, it would become sensitive to ampicillin. The vector was named as pRRS(2AsiSI).

The second plasmid constructed was pUCKm which contains one AsiSI site within the Km$^R$ gene. The vector was constructed from pUC19 and pGPS3. The resulting plasmid was used to clone the asiSIM gene in methylase selection.

2. Preparation of Genomic DNA and Restriction Digestion of Genomic DNA.

Genomic DNA was prepared from Arthrobacter speciece S (New England Biolabs collection #1221, originated from SibEnzyme, Russia) by the standard procedure consisting of the following steps:

a. cell lysis by addition of lysozyme (2 mg/ml final), sucrose (1% final), and 50 mM Tris-HCl, pH 8.0;
 b. cell lysis by addition of 10% SDS (final concentration 0.1%);
 c. cell lysis by addition of 1% Triton X-100 and 62 mM EDTA, 50 mM Tris-HCl, pH 8.0;
 d. phenol-CHCl$_3$ extraction of DNA 3 times (equal volume) and CHCl$_3$ extraction once;
 e. DNA dialysis in 4 liters of TE buffer, change 3 times; and
 f. RNA was removed by RNase A treatment and the genomic DNA was precipitated with 95% ethanol, spooled, washed, and resuspended in TE buffer.

Restriction enzymes NlaIII were diluted by 2-fold serial dilutions. Five to ten mg genomic DNA was digested partially with NlaIII at 37° C. for 30 min. The NlaIII digested genomic DNA was ligated to SphI digested and CIP treated pUCKm vector. The ligated DNA was used to transform ER2502 competent cells by the standard procedure.

AsiSI genomic DNA was also partially digested with Sau3AI and DNA fragment between 2–10 kb was gel-purified and then ligated to BamHI digested and CIP treated pRRS(2AsiSI). The ligated DNA was used to transform ER2502. AsiSI genomic DNA was also digested with AatII, AccI, AflIII, KasI, NdeI, or XmaI, respectively for construction of genomic DNA libraries.

3. Construction of NlaIII Partial Genomic DNA Libraries and and Selection of M.AsiSI by the Methylase Selection Method Methylase selection was performed for the AatII, AccI, AflIII, KasI, NdeI, and XmaI genomic DNA libraries and Sau3AI partial DNA library. AsiSI resistant clones were isolated from challenged transformants, but none of them showed any homology to C5 and N4C methylases. These resistant clones either came from contaminant DNA or had lost the AsiSI sites.

To avoid common Ap$^R$ vector contamination, Km$^R$ vector was constructed. For the transformation experiment the antibiotic kanamycin (Km) was used to select transformants of was libraries. A total of more than 2×10$^4$ Km$^R$ transformants were obtained in the transformation experiments. These transformants were pooled and amplified in 1 liter of overnight cultures. Plasmid DNA was prepared from the overnight cells by the Qiagen plasmid Maxi preparation kit. The plasmid library was challenged with AsiSI or SgfI followed by Mung Bean nuclease overnight at 37° C. The Mung Bean nuclease destroyed the ends and prevented the religation of cohesive ends. Following the digestion, the challenged DNA was transformed back into ER2502 cells. Km$^R$ survivors were screened for resistance to AsiSI/SgfI digestion. A total of 55 plasmid mini-preparations were made. Four clones (#3 in first batch, #8', #14', #22' in the second batch) were identified to be fully resistant to AsiSI/SgfI digestion. While other three in the first batch (#13, #14, #16) were partially resistant to the AsiSI/SgfI digestion. The four fully resistant clones (M.AsiSI positive) were sequenced using the universal primers for pUC19 multiple cloning sites. Part of the sequence of #14' was found to have high homology to C5 methylase. Part of the sequence of the #22' was also found to have high homology to C5 methylase in the conserved domains IX and X, normally at the C-terminus of the C5-methylase. Thus both ends of the methylase gene were found. Subsequent sequencing revealed whole asiSIM gene.

4. Restriction Mapping of the Flanking DNA of asiSIM Gene and Construction of More Genomic DNA Libraries Arthrobacter sp. S genomic DNA was digested with restriction enzymes with 5 or 6-bp recognition sequence to identify DNA fragments that encompass asiSIM gene and the flanking DNA. The genomic DNA was digested with AgeI, BamHI, BsaWI, BspEI, BsrFI, BstYI, EcoRI, KasI, NruI, NspI, PstI, PvuI, or SacI. The genomic DNA fragments were self-ligated, then used as the template for inverse PCR. Inverse PCR products were gel-purified and sequence. DNA sequences upstream and downstream were obtained and revealed new open reading frames. Four rounds of inverse PCR were performed to obtain about 1308 bp of downstream sequence. Comparison of the downstream sequence with known genes in Genbank indicated that one ORF has homology with pilus assembly protein and one partial ORF had homology with twitching mobility protein. It was concluded that the asiSIR gene may be located upstream of the M gene. The sequences of the inverse PCR primers were shown below:

Inverse PCR 1:
 5' TTTTTCTCAGGCCGCGAGCGAACA 3' (260–170) (SEQ ID NO:15)
 5' CGTCGATTCGCGAGTCCGGTGGTC 3' (260–171) (SEQ ID NO:16)

Inverse PCR 2:
 5' AGCGCGAGCCCCGAGGTGAGCATC 3' (262–40) (SEQ ID NO:17)
 5' CCTGCGGACCCTGACGATCCTGTC 3' (262–41) (SEQ ID NO:18)

Inverse PCR 3:
 5' GGTCCTTGAGGCCGACGCCCTTCT 3' (261–272) (SEQ ID NO:19)
 5' TCGCGATCATGTCGCGACAGGCCT 3' (261–273) (SEQ ID NO:20)

Inverse PCR 4:
 5' ATGGCGATCGGCGAGACGCCCATG 3' (262–130) (SEQ ID NO:21)
 5' CACCGAGGCGAAGGCCGGCACCGG 3' (262–131) (SEQ ID NO:22)

5. Cloning of asiSIM Gene into pACYC184 to Construct a Premodified Host

Two primers were synthesized with the following sequence:
 5'GGTGGTGGATCCGGAGGTAATAAAAT-GAATCGCGCAACTGCGGTCGAA TTG 3' (261–268) (SEQ ID NO:23)
 5' GGTGGTGCATGCTCATACGATCGAGGC-CACTACTTC 3' (261–141) (SEQ ID NO:24)

The asiSIM gene was amplified from the genomic DNA in PCR using primers 261–268 and 261–141 under PCR condition of 95° C. 1 min, 55° C. 1 min, 72° C. 1 min for 30 cycles. The PCR DNA was purified through a Qiagen spin column and digested with BamHI and SphI. The PCR fragment was purified again in low melting agarose gel and ligated to pACYC184 with compatible ends. After screening 18 plasmid mini-preparations, 14 clones were found to have the right size insertion fragment. Since there was no AsiSI site in the plasmid, four clones #1, #2, #3, #4 were cotransformed with the pRRS(2AsiSI) into ER2566. The pRRS (2AsiSI) plasmids were extracted again and one contransformed with #1, #3, #4 were found to be resistant to AsiSI digestion. The original pACYC-AsiSIM clone #1, #3, #4 were pooled. The premodified host ER2566 [pACYC-AsiSIM] was used for expression of the asiSIR gene in *E. coli*.

6. Cloning of asiSIR Gene by Inverse PCR

Two primers were synthesized with the following sequence:

5' ACTAGACGAAGTGAACGTGGCGGT 3' (260–168) (SEQ ID NO:25)

5' TCCGATTGACCCACTCCAGGCACA 3' (260–169) (SEQ ID NO:26)

The Genomic DNA was digested with AgeI, BamHI, BsaWI, BspEI, BsrFI, BstYI, EcoRI, KasI, NruI, NspI, PstI, PvuI, SacI separately. The digested DNA was ligated at a low DNA concentration at 2 μg/ml and then used for inverse PCR amplification of AsiSIR gene. Inverse PCR conditions were 95° C. 1 min, 55° C. 1 min, 72° C. 2 min for 35 cycles. Inverse PCR products were derived from AgeI, BsaWI, BstYI, and NruI templates, gel-purified from low-melting agarose and sequenced using primers 260–168 and 260–169. An ORF of 864 bp was found upstream of the asiSI gene. This ORF was the putative asiSIR gene (see section 7 below). It encodes a 287-amino acid protein with predicted molecular mass of 32.3 kDa.

7. Expression of asiSIR Gene in T7 Expression Vector pET21at

Two restriction sites (NdeI and HindIII) were incorporated into the forward and reverse primers, respectively. Two primers were synthesized to amplify the asiSI gene by PCR. The primers had the following sequence:

5' GGTGGTCATATGGGCGAGTCTATTGAT-CAATTAAAC 3' (261–164) (SEQ ID NO:27)

5' GGTGGTAAGCTTTCAGTCGGAGAGAAT-GAGGCGGTA 3' (261–165) (SEQ ID NO:28)

The asiSIR gene was amplified by PCR using Vent DNA polymerase and primers 261–164 and 261–165 under conditions of 95° C. 1 min, 55° C. 1 min, 72° C. 1 min for 25 cycles. The PCR product was purified by Qiagen spin column and digested with NdeI and HindIII. After purification, the PCR DNA was ligated to pET21at with compatible ends. The ligated DNA was transformed into premodified host ER2566 [pACYC-AsiSIM] and selected for $Ap^R$ $Cm^R$ transformants. Clones were cultured in 10 ml LB plus Ap and Cm and induced with IPTG (0.5 mM final) for 3 h. 48 cell extracts were assayed for activity. Eight clones (#10, #17, #19, #28, #31, #33, #35, #40) were highly active and another 7 clones (#5, #6, #12, #21, #22, #24, #36) had lower activity. The plasmids from highly active clones were sequenced, and the #28 was found to be the wild type and was used in the subsequent large scale purification.

8. Purification of AsiSI Endonuclease

Cell extract was prepared by sonication of 20 grams of IPTG-induced cells resuspended in 60 ml sonication buffer (50 mM Tris-HCl, pH 7.8, 10 mM β-mercaptoethanol). Cell debris was removed by centrifugation. The supernatant was loaded onto a Heparin Sepharose column. Fractions were eluted with a NaCl gradient from 0.05 M–1 M. Fractions containing AsiSI endonuclease as determined by an activity assay were pooled and dialyzed overnight in DEAE-Sepharose loading buffer (20 mM Tris-HCl, pH 7.5, 50 mM NaCl, 10 mM β-mercaptoethanol, 0.1 mM EDTA). After dialysis, the proteins were loaded onto a DEAE Sepharose column equilibrated with the same buffer. Fractions were eluted with a 0.05 M–1 M NaCl gradient and those fractions containing purified AsiSI were pooled. A total of 300,000 untis of functionally purified AsiSI were obtained.

The strain ER2566 [pACYC-AsiSIM, pET21at-AsiSIR] has been deposited under the terms and conditions of the Budapest Treaty with the American Type Culture Collection on Aug. 16, 2001 and received ATCC Accession No. PTA-3641

What is claimed is:

1. Isolated DNA coding for the AsiSI restriction endonuclease, wherein the isolated DNA is obtainable from ATCC No. PTA-3641.

2. A recombinant DNA vector comprising a vector into which a DNA segment encoding the AsiSI restriction endonuclease gene has been inserted.

3. Isolated DNA encoding the AsiSI restriction endonuclease and AsiSI methylase, wherein the isolated DNA is obtainable from ATCC No. PTA-3641.

4. A vector which comprises the isolated DNA of claim 3.

5. A host cell transformed by the vector of claims 2, or 4.

6. A method of producing recombinant AsiSI restriction endonuclease comprising culturing a host cell transformed with the vector of claims 2, or 4 under conditions suitable for expression of said endonuclease.

* * * * *

UNITED STATES PATENT AND TRADEMARK OFFICE
CERTIFICATE OF CORRECTION

PATENT NO.    : 6,514,737 B1                                                Page 1 of 1
DATED         : February 4, 2003
INVENTOR(S)   : Zhu et al.

It is certified that error appears in the above-identified patent and that said Letters Patent is hereby corrected as shown below:

Column 2,
Line 49, replace "Baidauf" with -- Baldauf --

Column 5,
Line 22, replace "KM$^R$" with -- Km$^R$ --

Column 6,
Line 31, replace "pET2 at" with -- pET21at --
Line 33, replace "APR CmR" with -- Ap$^R$ Cm$^R$ --
Line 62, replace "PRRS" with -- pRRS --

Column 7,
Line 52, replace "of was libraries" with -- of *Nla*III libraries --

Signed and Sealed this

Eighth Day of July, 2003

JAMES E. ROGAN
*Director of the United States Patent and Trademark Office*

SEQUENCE LISTING

<160> NUMBER OF SEQ ID NOS: 29

<210> SEQ ID NO 1
<211> LENGTH: 8
<212> TYPE: DNA
<213> ORGANISM: Arthrobacter sp.

<400> SEQUENCE: 1 gcgatcgc                                                          8

<210> SEQ ID NO 2
<211> LENGTH: 6
<212> TYPE: DNA
<213> ORGANISM: Deinococcus radiophilus

<400> SEQUENCE: 2 tttaaa                                                            6

<210> SEQ ID NO 3
<211> LENGTH: 9
<212> TYPE: DNA

```
<213> ORGANISM: Deinococcus radiophilus
<220> FEATURE:
<221> NAME/KEY: misc_feature
<222> LOCATION: (4)..(6)
<223> OTHER INFORMATION: N= G, A, C or T

<400> SEQUENCE: 3 cacnnngtg                                                                  9

<210> SEQ ID NO 4
<211> LENGTH: 6
<212> TYPE: DNA
<213> ORGANISM: Escherichia coli

<400> SEQUENCE: 4 gaattc                                                                     6

<210> SEQ ID NO 5
<211> LENGTH: 5
<212> TYPE: DNA
<213> ORGANISM: Escherichia coli
<220> FEATURE:
<221> NAME/KEY: misc_feature
<222> LOCATION: (3)
<223> OTHER INFORMATION: W = A or T

<400> SEQUENCE: 5 ccwgg                                                                      5

<210> SEQ ID NO 6
<211> LENGTH: 8
<212> TYPE: DNA
<213> ORGANISM: Nocardia otitidis-caviarum

<400> SEQUENCE: 6 gcggccgc                                                                   8

<210> SEQ ID NO 7
<211> LENGTH: 1173
<212> TYPE: DNA
<213> ORGANISM: Arthrobacter sp.
<220> FEATURE:
<221> NAME/KEY: CDS
<222> LOCATION: (1)..(1173)

<400> SEQUENCE: 7 gtg aat cgc gca act gcg gtc gaa ttg ttt gcg ggc tgt ggg ggg cta         48
Val Asn Arg Ala Thr Ala Val Glu Leu Phe Ala Gly Cys Gly Gly Leu
 1               5                  10                  15 tcg acc gga ctg ttg gac gct ggc tac gac gtg cgt ctg ggt gtc gac         96
Ser Thr Gly Leu Leu Asp Ala Gly Tyr Asp Val Arg Leu Gly Val Asp
            20                  25                  30 aac aat gcc cca agt ttg gtc gcc tat gat tac aac cat gcc tat cgg        144
Asn Asn Ala Pro Ser Leu Val Ala Tyr Asp Tyr Asn His Ala Tyr Arg
        35                  40                  45 ggg tca aag tca cta ctc cgc gat gtt agt gcc tta agg gga ccc gaa        192
Gly Ser Lys Ser Leu Leu Arg Asp Val Ser Ala Leu Arg Gly Pro Glu
    50                  55                  60 cta ctg gaa gcc gca gga gtc gac tcg att gac gta ctc tcc ggc ggg        240
Leu Leu Glu Ala Ala Gly Val Asp Ser Ile Asp Val Leu Ser Gly Gly
65                  70                  75                  80 ccg ccc tgc cag ccc ttt tcg ata gcc ggg aag cga ctg ggg ctt gac        288
Pro Pro Cys Gln Pro Phe Ser Ile Ala Gly Lys Arg Leu Gly Leu Asp
                85                  90                  95
```

```
gat cct cga ggg cac ctt att gcg gaa ttt gtc cgg att gta gac gaa      336
Asp Pro Arg Gly His Leu Ile Ala Glu Phe Val Arg Ile Val Asp Glu
        100                 105                 110 gtt cgg ccg aag gcg gtc gtg ttt gaa aac gta cct gca ctg caa act      384
Val Arg Pro Lys Ala Val Val Phe Glu Asn Val Pro Ala Leu Gln Thr
    115                 120                 125 tcg cat aat gga gat gta gtt cgc gca aca act gac gcg ctt gag cag      432
Ser His Asn Gly Asp Val Val Arg Ala Thr Thr Asp Ala Leu Glu Gln
130                 135                 140 ctt ggc tac ggg gta aga cgc gca atc ctc aac gcg gcc gac tgg ggt      480
Leu Gly Tyr Gly Val Arg Arg Ala Ile Leu Asn Ala Ala Asp Trp Gly
145                 150                 155                 160 gtc ccg cag gcg cgc aag cga ttg atc ctg att gct gtg cgc gac gta      528
Val Pro Gln Ala Arg Lys Arg Leu Ile Leu Ile Ala Val Arg Asp Val
        165                 170                 175 gca gag ttt tcg ttc ccg cct aag ccg act cac tca ggc gac ccg tct      576
Ala Glu Phe Ser Phe Pro Pro Lys Pro Thr His Ser Gly Asp Pro Ser
            180                 185                 190 ggg agc ctt cgg ccc tac cga aca gct tcg gat gct cta tgg gac ctg      624
Gly Ser Leu Arg Pro Tyr Arg Thr Ala Ser Asp Ala Leu Trp Asp Leu
        195                 200                 205 cct gac gtg aac acg gat gct gcc cgt gag ata ccg aac cac gaa ccg      672
Pro Asp Val Asn Thr Asp Ala Ala Arg Glu Ile Pro Asn His Glu Pro
210                 215                 220 act gcc cat tcg ccc gcg atg ctc aag gct ttc gcc gga cta gaa ccg      720
Thr Ala His Ser Pro Ala Met Leu Lys Ala Phe Ala Gly Leu Glu Pro
225                 230                 235                 240 ggg aag cgt gaa ccg aag tcg cgg cac gac agg ctg cat ccc gac cgc      768
Gly Lys Arg Glu Pro Lys Ser Arg His Asp Arg Leu His Pro Asp Arg
            245                 250                 255 ccg ggg tat act ctt cgc gca ggc tct ggc aac ttc tca cca atg agg      816
Pro Gly Tyr Thr Leu Arg Ala Gly Ser Gly Asn Phe Ser Pro Met Arg
        260                 265                 270 ccg atc cat tat gag ttt gat cgg gtg att tcg gtt cga gag agt gct      864
Pro Ile His Tyr Glu Phe Asp Arg Val Ile Ser Val Arg Glu Ser Ala
        275                 280                 285 cgg tta cag ggc ttt agc gat gac ttc atc tgg ccg gac agc ctg tcc      912
Arg Leu Gln Gly Phe Ser Asp Asp Phe Ile Trp Pro Asp Ser Leu Ser
290                 295                 300 aga ctt caa caa tac cgt caa gtt gga aac gct gtt ccg cca gct ctt      960
Arg Leu Gln Gln Tyr Arg Gln Val Gly Asn Ala Val Pro Pro Ala Leu
305                 310                 315                 320 ggg gag gtg gtc ggg cga cac gtt gcg tcg att ctg gga ttt gac ctt     1008
Gly Glu Val Val Gly Arg His Val Ala Ser Ile Leu Gly Phe Asp Leu
            325                 330                 335 gat gct gat tca gca gcg gga gac cct gct tcg cgg ccg aat ccg ttc     1056
Asp Ala Asp Ser Ala Ala Gly Asp Pro Ala Ser Arg Pro Asn Pro Phe
        340                 345                 350 aac ttc aca cac gaa gag cgt gca gct cga cgg gcg cgt tac cac cgg     1104
Asn Phe Thr His Glu Glu Arg Ala Ala Arg Arg Ala Arg Tyr His Arg
        355                 360                 365 ggt gga gcg agt ttc gga tcg gcc aac gga gcg tcc gac tcc tcg gaa     1152
Gly Gly Ala Ser Phe Gly Ser Ala Asn Gly Ala Ser Asp Ser Ser Glu
370                 375                 380 gta gtg gcc tcg atc gta tga                                         1173
Val Val Ala Ser Ile Val
385                 390

<210> SEQ ID NO 8
<211> LENGTH: 390
```

-continued

```
<212> TYPE: PRT
<213> ORGANISM: Arthrobacter sp.

<400> SEQUENCE: 8

Val Asn Arg Ala Thr Ala Val Glu Leu Phe Ala Gly Cys Gly Gly Leu
 1               5                  10                  15

Ser Thr Gly Leu Leu Asp Ala Gly Tyr Asp Val Arg Leu Gly Val Asp
            20                  25                  30

Asn Asn Ala Pro Ser Leu Val Ala Tyr Asp Tyr Asn His Ala Tyr Arg
        35                  40                  45

Gly Ser Lys Ser Leu Leu Arg Asp Val Ser Ala Leu Arg Gly Pro Glu
    50                  55                  60

Leu Leu Glu Ala Ala Gly Val Asp Ser Ile Asp Val Leu Ser Gly Gly
65                  70                  75                  80

Pro Pro Cys Gln Pro Phe Ser Ile Ala Gly Lys Arg Leu Gly Leu Asp
                85                  90                  95

Asp Pro Arg Gly His Leu Ile Ala Glu Phe Val Arg Ile Val Asp Glu
            100                 105                 110

Val Arg Pro Lys Ala Val Val Phe Glu Asn Val Pro Ala Leu Gln Thr
        115                 120                 125

Ser His Asn Gly Asp Val Val Arg Ala Thr Thr Asp Ala Leu Glu Gln
    130                 135                 140

Leu Gly Tyr Gly Val Arg Arg Ala Ile Leu Asn Ala Ala Asp Trp Gly
145                 150                 155                 160

Val Pro Gln Ala Arg Lys Arg Leu Ile Leu Ile Ala Val Arg Asp Val
                165                 170                 175

Ala Glu Phe Ser Phe Pro Pro Lys Pro Thr His Ser Gly Asp Pro Ser
            180                 185                 190

Gly Ser Leu Arg Pro Tyr Arg Thr Ala Ser Asp Ala Leu Trp Asp Leu
        195                 200                 205

Pro Asp Val Asn Thr Asp Ala Ala Arg Glu Ile Pro Asn His Glu Pro
    210                 215                 220

Thr Ala His Ser Pro Ala Met Leu Lys Ala Phe Ala Gly Leu Glu Pro
225                 230                 235                 240

Gly Lys Arg Glu Pro Lys Ser Arg His Asp Arg Leu His Pro Asp Arg
                245                 250                 255

Pro Gly Tyr Thr Leu Arg Ala Gly Ser Gly Asn Phe Ser Pro Met Arg
            260                 265                 270

Pro Ile His Tyr Glu Phe Asp Arg Val Ile Ser Val Arg Glu Ser Ala
        275                 280                 285

Arg Leu Gln Gly Phe Ser Asp Asp Phe Ile Trp Pro Asp Ser Leu Ser
    290                 295                 300

Arg Leu Gln Gln Tyr Arg Gln Val Gly Asn Ala Val Pro Pro Ala Leu
305                 310                 315                 320

Gly Glu Val Val Gly Arg His Val Ala Ser Ile Leu Gly Phe Asp Leu
                325                 330                 335

Asp Ala Asp Ser Ala Ala Gly Asp Pro Ala Ser Arg Pro Asn Pro Phe
            340                 345                 350

Asn Phe Thr His Glu Glu Arg Ala Ala Arg Ala Arg Tyr His Arg
        355                 360                 365

Gly Gly Ala Ser Phe Gly Ser Ala Asn Gly Ala Ser Asp Ser Ser Glu
    370                 375                 380

Val Val Ala Ser Ile Val
385                 390
```

-continued

```
<210> SEQ ID NO 9
<211> LENGTH: 864
<212> TYPE: DNA
<213> ORGANISM: Arthrobacter sp.
<220> FEATURE:
<221> NAME/KEY: CDS
<222> LOCATION: (1)..(864)

<400> SEQUENCE: 9 atg ggc gag tct att gat caa tta aac cct atc tcc ggg gac ggt cgc      48
Met Gly Glu Ser Ile Asp Gln Leu Asn Pro Ile Ser Gly Asp Gly Arg
 1               5                  10                  15 ctc ctg caa tct cac ggt ctg acc agc aag gta tac gtt ccg ata ttg      96
Leu Leu Gln Ser His Gly Leu Thr Ser Lys Val Tyr Val Pro Ile Leu
             20                  25                  30 cga tac gtg ttt gcg ctt cgc tac aaa act ggc gac acg gtc gtc gaa     144
Arg Tyr Val Phe Ala Leu Arg Tyr Lys Thr Gly Asp Thr Val Val Glu
         35                  40                  45 ttc acc ctt gat gac ata agg gac gcg gct gcg gcc ctg ggt ata gtg     192
Phe Thr Leu Asp Asp Ile Arg Asp Ala Ala Ala Ala Leu Gly Ile Val
     50                  55                  60 gta cgt aat gcc gct gac gtg ata tat agg atg aga tca cgc acc gtc     240
Val Arg Asn Ala Ala Asp Val Ile Tyr Arg Met Arg Ser Arg Thr Val
 65                  70                  75                  80 ctt ccg gct gag atc ctt gag ctt ggg ttt tac gtc ctc aca caa gct     288
Leu Pro Ala Glu Ile Leu Glu Leu Gly Phe Tyr Val Leu Thr Gln Ala
                 85                  90                  95 ggt cga ggc cgc tat cga ttt gag cag gca tcc agc act gtt atc gac     336
Gly Arg Gly Arg Tyr Arg Phe Glu Gln Ala Ser Ser Thr Val Ile Asp
            100                 105                 110 cta cct aat aca agg cca ata gaa gcc ctc gac ttg aca cca aac ccc     384
Leu Pro Asn Thr Arg Pro Ile Glu Ala Leu Asp Leu Thr Pro Asn Pro
        115                 120                 125 gtt cga cgt tta ctc cca gaa cac tta gcc gac atg gat gag cag gcg     432
Val Arg Arg Leu Leu Pro Glu His Leu Ala Asp Met Asp Glu Gln Ala
    130                 135                 140 att ctg atg gtc gcc gga tac tgc aat ctg tgg cag cat ttc aca ggg     480
Ile Leu Met Val Ala Gly Tyr Cys Asn Leu Trp Gln His Phe Thr Gly
145                 150                 155                 160 ctt aca gtc tac cgg ctg cgt tct cat gtc cga aaa agt gtg cct gga     528
Leu Thr Val Tyr Arg Leu Arg Ser His Val Arg Lys Ser Val Pro Gly
                165                 170                 175 gtg ggt caa gcg gaa cta gac gaa gtg aac gtg gcg gtc gcg gta cgg     576
Val Gly Gln Ala Glu Leu Asp Glu Val Asn Val Ala Val Ala Val Arg
            180                 185                 190 gat gac gag gtg ccg gtg atc atc cca gtc gaa gcg aag gct gtc gcg     624
Asp Asp Glu Val Pro Val Ile Ile Pro Val Glu Ala Lys Ala Val Ala
        195                 200                 205 gat ccg gtg aac cga gta cag att gca act cag gtt gcc ttc gcg aac     672
Asp Pro Val Asn Arg Val Gln Ile Ala Thr Gln Val Ala Phe Ala Asn
    210                 215                 220 cgg tat ttt gct gag cac gaa ttt cgc cca atg act atc aaa gtc gat     720
Arg Tyr Phe Ala Glu His Glu Phe Arg Pro Met Thr Ile Lys Val Asp
225                 230                 235                 240 cgg gat agt gtc ctc aat ctg ctc gaa ttt aat gcc acc cct att gca     768
Arg Asp Ser Val Leu Asn Leu Leu Glu Phe Asn Ala Thr Pro Ile Ala
                245                 250                 255 agc gag ata gag gtt att cgg tca gct aga tac cgc ctc att ctc tcc     816
Ser Glu Ile Glu Val Ile Arg Ser Ala Arg Tyr Arg Leu Ile Leu Ser
            260                 265                 270
```

```
gac aga cag cgc cac ctt atc gac gaa aca gac cag gtg atg ttg tga    864
Asp Arg Gln Arg His Leu Ile Asp Glu Thr Asp Gln Val Met Leu
        275                 280                 285
```

<210> SEQ ID NO 10
<211> LENGTH: 287
<212> TYPE: PRT
<213> ORGANISM: Arthrobacter sp.

<400> SEQUENCE: 10

```
Met Gly Glu Ser Ile Asp Gln Leu Asn Pro Ile Ser Gly Asp Gly Arg
 1               5                  10                  15

Leu Leu Gln Ser His Gly Leu Thr Ser Lys Val Tyr Val Pro Ile Leu
             20                  25                  30

Arg Tyr Val Phe Ala Leu Arg Tyr Lys Thr Gly Asp Thr Val Val Glu
         35                  40                  45

Phe Thr Leu Asp Asp Ile Arg Asp Ala Ala Ala Leu Gly Ile Val
     50                  55                  60

Val Arg Asn Ala Ala Asp Val Ile Tyr Arg Met Arg Ser Arg Thr Val
 65                  70                  75                  80

Leu Pro Ala Glu Ile Leu Glu Leu Gly Phe Tyr Val Leu Thr Gln Ala
                 85                  90                  95

Gly Arg Gly Arg Tyr Arg Phe Glu Gln Ala Ser Ser Thr Val Ile Asp
            100                 105                 110

Leu Pro Asn Thr Arg Pro Ile Glu Ala Leu Asp Leu Thr Pro Asn Pro
        115                 120                 125

Val Arg Arg Leu Leu Pro Glu His Leu Ala Asp Met Asp Glu Gln Ala
    130                 135                 140

Ile Leu Met Val Ala Gly Tyr Cys Asn Leu Trp Gln His Phe Thr Gly
145                 150                 155                 160

Leu Thr Val Tyr Arg Leu Arg Ser His Val Arg Lys Ser Val Pro Gly
                165                 170                 175

Val Gly Gln Ala Glu Leu Asp Glu Val Asn Val Ala Val Ala Val Arg
            180                 185                 190

Asp Asp Glu Val Pro Val Ile Pro Val Glu Ala Lys Ala Val Ala
        195                 200                 205

Asp Pro Val Asn Arg Val Gln Ile Ala Thr Gln Val Ala Phe Ala Asn
    210                 215                 220

Arg Tyr Phe Ala Glu His Glu Phe Arg Pro Met Thr Ile Lys Val Asp
225                 230                 235                 240

Arg Asp Ser Val Leu Asn Leu Leu Glu Phe Asn Ala Thr Pro Ile Ala
                245                 250                 255

Ser Glu Ile Glu Val Ile Arg Ser Ala Arg Tyr Arg Leu Ile Leu Ser
            260                 265                 270

Asp Arg Gln Arg His Leu Ile Asp Glu Thr Asp Gln Val Met Leu
        275                 280                 285
```

<210> SEQ ID NO 11
<211> LENGTH: 12
<212> TYPE: DNA
<213> ORGANISM: Arthrobacter sp.

<400> SEQUENCE: 11
aagcgatcgc tt    12

<210> SEQ ID NO 12
<211> LENGTH: 6

```
<212> TYPE: PRT
<213> ORGANISM: C5 METHYLASE MOTIF I

<400> SEQUENCE: 12

Leu Phe Ala Gly Ile Gly
  1               5

<210> SEQ ID NO 13
<211> LENGTH: 6
<212> TYPE: PRT
<213> ORGANISM: C5 METHYLASE MOTIF I

<400> SEQUENCE: 13

Leu Phe Ser Gly Ile Gly
  1               5

<210> SEQ ID NO 14
<211> LENGTH: 6
<212> TYPE: PRT
<213> ORGANISM: C5 METHYLASE MOTIF IV

<400> SEQUENCE: 14

Glu Asn Val Arg Gly Leu
  1               5

<210> SEQ ID NO 15
<211> LENGTH: 24
<212> TYPE: DNA
<213> ORGANISM: Arthrobacter sp.

<400> SEQUENCE: 15
tttttctcag gccgcgagcg aaca                                              24

<210> SEQ ID NO 16
<211> LENGTH: 24
<212> TYPE: DNA
<213> ORGANISM: Arthrobacter sp.

<400> SEQUENCE: 16
cgtcgattcg cgagtccggt ggtc                                              24

<210> SEQ ID NO 17
<211> LENGTH: 24
<212> TYPE: DNA
<213> ORGANISM: Arthrobacter sp.

<400> SEQUENCE: 17
agcgcgagcc ccgaggtgag catc                                              24

<210> SEQ ID NO 18
<211> LENGTH: 24
<212> TYPE: DNA
<213> ORGANISM: Arthrobacter sp.

<400> SEQUENCE: 18
cctgcggacc ctgacgatcc tgtc                                              24

<210> SEQ ID NO 19
<211> LENGTH: 24
<212> TYPE: DNA
<213> ORGANISM: Arthrobacter sp.

<400> SEQUENCE: 19
ggtccttgag gccgacgccc ttct                                              24
```

-continued

```
<210> SEQ ID NO 20
<211> LENGTH: 24
<212> TYPE: DNA
<213> ORGANISM: Arthrobacter sp.

<400> SEQUENCE: 20
tcgcgatcat gtcgcgacag gcct                                              24

<210> SEQ ID NO 21
<211> LENGTH: 24
<212> TYPE: DNA
<213> ORGANISM: Arthrobacter sp.

<400> SEQUENCE: 21
atggcgatcg gcgagacgcc catg                                              24

<210> SEQ ID NO 22
<211> LENGTH: 24
<212> TYPE: DNA
<213> ORGANISM: Arthrobacter sp.

<400> SEQUENCE: 22
caccgaggcg aaggccggca ccgg                                              24

<210> SEQ ID NO 23
<211> LENGTH: 51
<212> TYPE: DNA
<213> ORGANISM: Arthrobacter sp.

<400> SEQUENCE: 23
ggtggtggat ccggaggtaa taaaatgaat cgcgcaactg cggtcgaatt g                51

<210> SEQ ID NO 24
<211> LENGTH: 36
<212> TYPE: DNA
<213> ORGANISM: Arthrobacter sp.

<400> SEQUENCE: 24
ggtggtgcat gctcatacga tcgaggccac tacttc                                 36

<210> SEQ ID NO 25
<211> LENGTH: 24
<212> TYPE: DNA
<213> ORGANISM: Arthrobacter sp.

<400> SEQUENCE: 25
actagacgaa gtgaacgtgg cggt                                              24

<210> SEQ ID NO 26
<211> LENGTH: 24
<212> TYPE: DNA
<213> ORGANISM: Arthrobacter sp.

<400> SEQUENCE: 26
tccgattgac ccactccagg caca                                              24

<210> SEQ ID NO 27
<211> LENGTH: 36
<212> TYPE: DNA
<213> ORGANISM: Arthrobacter sp.

<400> SEQUENCE: 27
ggtggtcata tgggcgagtc tattgatcaa ttaaac                                 36
```

```
<210> SEQ ID NO 28
<211> LENGTH: 36
<212> TYPE: DNA
<213> ORGANISM: Arthrobacter sp.

<400> SEQUENCE: 28
ggtggtaagc tttcagtcgg agagaatgag gcggta                          36

<210> SEQ ID NO 29
<211> LENGTH: 5
<212> TYPE: DNA
<213> ORGANISM: Deinococcus radiophilus
<220> FEATURE:
<221> NAME/KEY: misc_feature
<222> LOCATION: (3)
<223> OTHER INFORMATION: N=G, A, C or T

<400> SEQUENCE: 29 ggncc                                                             5
```